United States Patent [19]

Brown et al.

[11] Patent Number: 5,178,277
[45] Date of Patent: Jan. 12, 1993

[54] BREATHER POUCH FOR SURGICAL SUTURE PACKAGES

[75] Inventors: David L. Brown, Wallingford; Stanley J. Malinowski, Guilford, both of Conn.

[73] Assignee: United States Surgical Corporation, Norwalk, Conn.

[21] Appl. No.: 891,924

[22] Filed: Jun. 1, 1992

Related U.S. Application Data

[63] Continuation of Ser. No. 780,776, Oct. 22, 1991, abandoned, which is a continuation of Ser. No. 637,488, Jan. 4, 1991, abandoned.

[51] Int. Cl.⁵ .................... A61B 17/06; A61B 19/02; B65D 73/00
[52] U.S. Cl. ................... 206/439; 206/484.1; 206/813; 156/289; 156/291
[58] Field of Search .............. 206/439, 813, 484.1; 156/289, 291

[56] References Cited

U.S. PATENT DOCUMENTS

| | | |
|---|---|---|
| 2,917,878 | 12/1959 | Carnarius et al. |
| 2,965,225 | 12/1960 | Zoller et al. |
| 3,043,067 | 7/1962 | Rynkiewicz et al. |
| 3,143,209 | 8/1964 | Turiansky |
| 3,147,861 | 9/1964 | Kurtz |
| 3,163,288 | 12/1964 | Arvidsson |
| 3,189,174 | 6/1965 | Cormack |
| 3,202,273 | 8/1965 | Riall |
| 3,221,873 | 12/1965 | Bowes et al. |
| 3,256,981 | 6/1966 | Kurtz |
| 3,280,971 | 10/1966 | Regan, Jr. |
| 3,301,392 | 1/1967 | Regan, Jr. |
| 3,315,802 | 4/1967 | Lonholdt et al. |
| 3,338,019 | 8/1967 | Trewella et al. |
| 3,357,549 | 12/1967 | Staiti |
| 3,419,137 | 12/1968 | Walck, III |
| 3,490,192 | 1/1970 | Regan, Jr. |
| 3,509,991 | 5/1970 | Hurst ........................ 206/813 X |
| 3,613,879 | 10/1971 | Kemble |
| 3,642,126 | 2/1972 | Kurtz |
| 3,648,949 | 3/1972 | Berger et al. |
| 3,728,839 | 4/1973 | Glick |
| 3,731,793 | 5/1973 | Hagel |
| 3,815,315 | 6/1974 | Glick |
| 3,876,068 | 4/1975 | Sonnino |
| 3,903,335 | 9/1975 | Jones |
| 3,910,410 | 10/1975 | Shaw ........................ 206/813 X |
| 3,926,311 | 12/1975 | Laske |
| 3,939,969 | 2/1976 | Miller et al. |
| 3,951,261 | 4/1976 | Mandel et al. |
| 3,954,174 | 5/1976 | Kraus |
| 3,991,881 | 11/1976 | Augurt |
| 3,995,739 | 12/1976 | Tasch et al. |
| 4,014,433 | 3/1977 | Cerwin |
| 4,063,638 | 12/1977 | Marwood |
| 4,069,912 | 1/1978 | Black et al. |
| 4,089,410 | 5/1978 | Bolanowski et al. |
| 4,125,985 | 11/1978 | Laske ........................ 206/439 |
| 4,131,195 | 12/1978 | Worrell, Sr. |
| 4,135,622 | 1/1979 | Glick |
| 4,168,000 | 9/1979 | MacRitchie |
| 4,253,563 | 3/1981 | Komarnycky |
| 4,261,463 | 4/1981 | Shave |
| 4,284,194 | 8/1981 | Flatau |
| 4,363,319 | 12/1982 | Altshuler |
| 4,365,716 | 12/1982 | Watt |
| 4,367,816 | 1/1983 | Wilkes ........................ 206/439 |
| 4,369,880 | 1/1983 | Giggey et al. |
| 4,406,363 | 9/1983 | Aday |

(List continued on next page.)

FOREIGN PATENT DOCUMENTS 0322199 6/1989 European Pat. Off.

Primary Examiner—William I. Price
Attorney, Agent, or Firm—Thomas R. Bremer; Peter G. Dilworth; Rocco S. Barrese

[57] ABSTRACT

A breather package for surgical elements such as sutures or suture-needle assemblies having a layer of fibrous material and a layer of plastic material forming a pocket therebetween. Longitudinal heat seals and transverse top and bottom seals are provided which form the package. The layer of fibrous material is provided with longitudinal strips of release agent material through which the longitudinal heat seals are formed. An apparatus for forming such a package is also disclosed.

27 Claims, 3 Drawing Sheets

U.S. PATENT DOCUMENTS

| | | |
|---|---|---|
| 4,412,614 | 11/1983 | Ivanov et al. . |
| 4,412,617 | 11/1983 | Cerwin . |
| 4,424,898 | 1/1984 | Thyen et al. . |
| 4,427,109 | 1/1984 | Roshdy . |
| 4,491,218 | 1/1985 | Aday . |
| 4,519,501 | 5/1985 | Cerwin . |
| 4,549,649 | 10/1985 | Roshdy . |
| 4,555,016 | 11/1985 | Aday et al. . |
| 4,603,538 | 8/1986 | Shave . |
| 4,630,729 | 12/1986 | Hirt et al. ............... 206/813 X |
| 4,708,241 | 11/1987 | Black . |
| 4,961,498 | 10/1990 | Kalinski et al. . |
| 4,962,856 | 10/1990 | Carter ............... 206/439 |

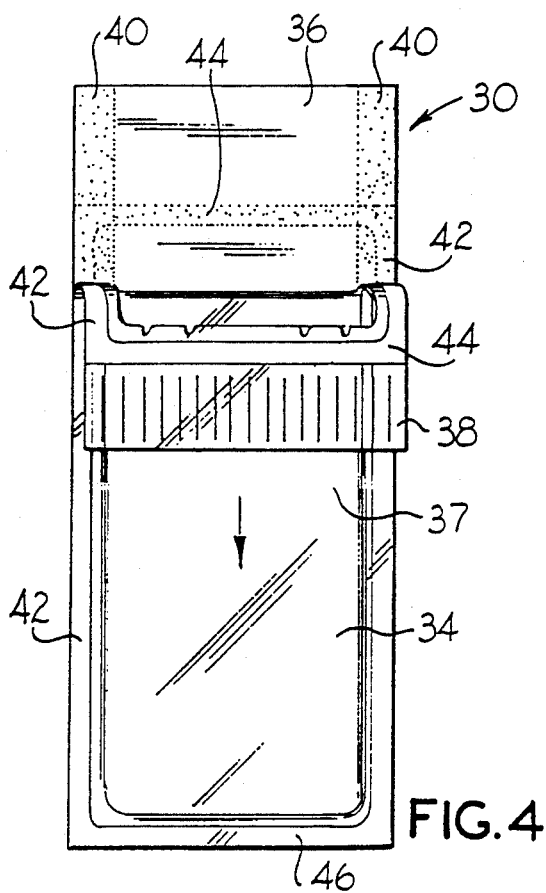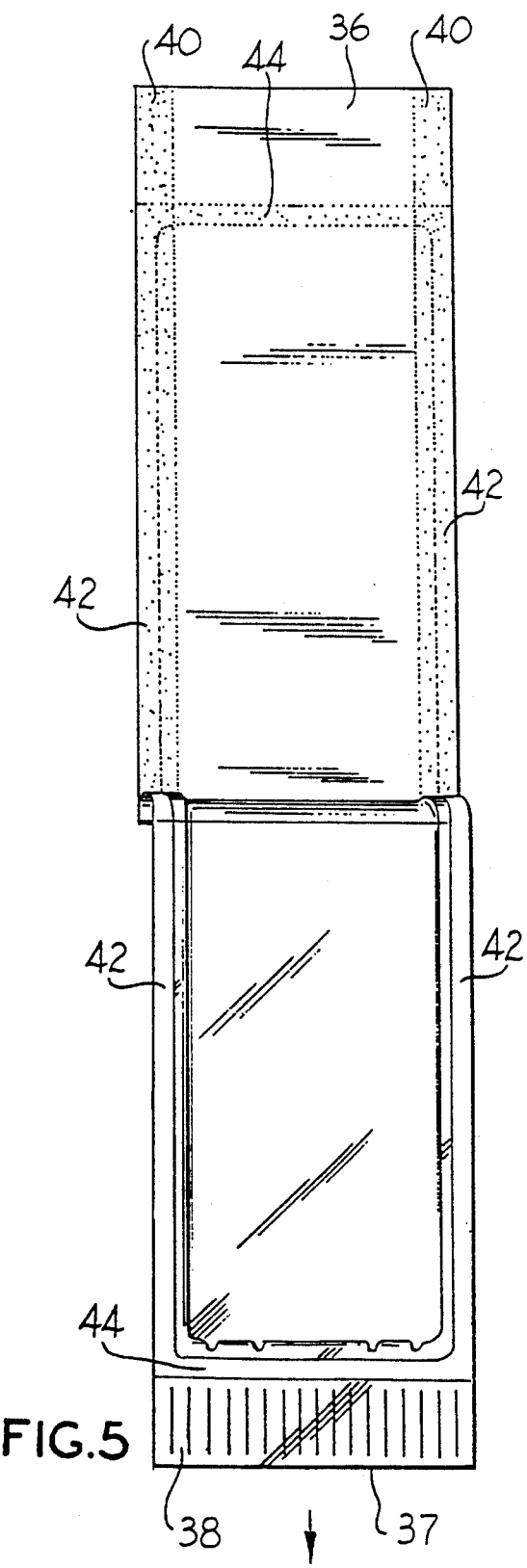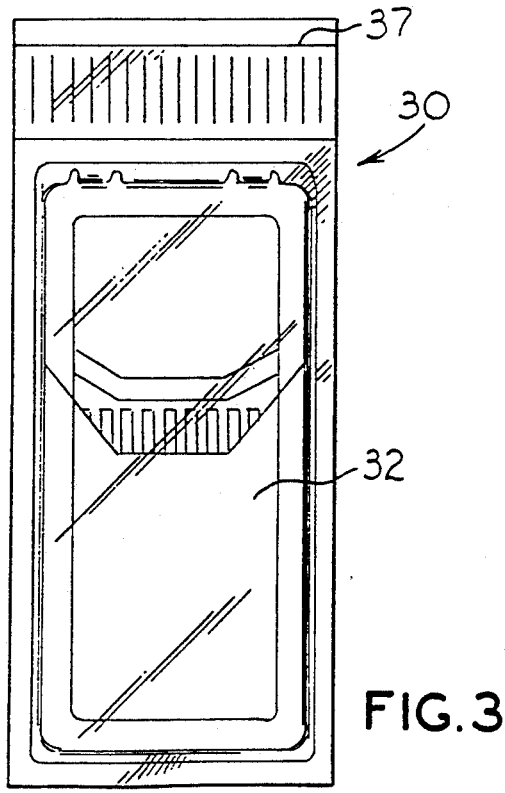
FIG.4
FIG.5
FIG.3

BREATHER POUCH FOR SURGICAL SUTURE PACKAGES

This is a continuation of copending application Ser. No. 07/780,776, filed on Oct. 22, 1991, which is a file wrapper continuation of U.S. Ser. No. 07/637,488, filed on Jan. 4, 1991 now abandoned.

BACKGROUND OF THE INVENTION

1. Field of the Invention

The present invention relates to packaging devices for surgical elements, and more particularly to breather pouches for enclosing surgical suture-needle packages.

2. Discussion of the Prior Art

Breather packages for packaging surgical elements in which a sheet of clear plastic is adhered to a paper, cardboard or other fibrous material backing to provide a sterile display environment for the surgical device are well known in the art. These breather packages generally enclose a sterilized package of surgical devices or elements, such as needles or suture-needle assemblies. The surgical package is fit between the fibrous material backing and the plastic layer and the plastic is then sealed to the fibrous layer to completely enclose the surgical package.

However, while the assembly process of such a package generally provides a secure package which is aesthetically pleasing as a final end product display package, several distinct problems occur upon opening the package, particularly within the sterile environment of an operating room. One of the more popular packaging materials for use in the surgical suture and surgical instrument field is a material known as Tyvek (a registered trademark of DuPont), which is a fibrous material constructed of spunbonded polyolefin, in which the polyolefin fibers are spun into a web and compressed to form a high strength porous material. It is common to use Tyvek as the backing material for the breather pouch, whereby the outer layer of plastic material is heat sealed to the edges of the Tyvek sheet to secure the suture package therebetween.

A distinct disadvantage concerning packages formed in this manner, as well as any package including a fibrous material such as Tyvek, cardboard, fiberboard, paper or the like, lies in the fact that when the plastic layer is adhered to the fibrous layer, whether by means of adhesives, heat seals or any other method, upon removing the plastic layer from the fibrous layer there is a tendency for the fibrous layer to separate from itself so that the fibers pull apart from each other. This occurrence, known as "fiber-pull", is similar to a delamination of the layers and occurs at the edges of the fibrous layer where the ends of the fibers are exposed. As the plastic layer is peeled back for removal from the fibrous layer, fiber-pull generally occurs at the edges and results in the continued encapsulation of the package disposed within the breather pouch.

This occurrence of fiber-pull can create two problems in an operating room during surgery. The most important problem is the fact that upon pulling the plastic layer from the fiber layer, if the suture package is still encapsulated in the breather pouch, it requires the surgical team member to further attempt to open the package which may result in a critical delay which may affect the health of the patient. Furthermore, in order to open such a package after the fiber layer has been removed, a sharp instrument may sometimes be necessary to puncture the pouch to get at the package inside. This will require the use of an instrument which has previously been sterilized, and whose sterility may be compromised in order to open the package.

A second problem resulting from the occurrence of fiber-pull is the fact that a large amount of clutter would result in the operating room if a significant number of sutures are required. Again, since the operating room is a sterile environment, the presence of a large number of torn pieces of fibrous paper, as well as particulate fibers which separate from the Tyvek, will be a detriment to the sterile conditions which are required.

In order to overcome the fiber-pull problem, in the prior art there are packages having a Tyvek layer adhered to a plastic layer through the provision of a release agent which is applied to the surface of the Tyvek layer which faces the plastic layer. The entire surface of the Tyvek material is coated with the release agent, which provides for a pull force to separate the plastic from the Tyvek which is lower than the pull force required to separate the fibers from themselves in the Tyvek layer. In general, after the release agent is applied to the Tyvek layer, the surgical suture package is positioned on the Tyvek and then the plastic layer is heat sealed through the release agent to the Tyvek about the periphery of the package.

This construction, while reducing the possibility of fiber-pull and its associated encapsulation problems, also suffers several disadvantages. A significant disadvantage is the increased cost required to produce the breather pouch, since an extensive amount of release agent material is used to cover the entire surface of the Tyvek layer. These release agents generally comprise adhesive materials which adhere to the Tyvek layer and dry to a nontacky finish.

A second important disadvantage lies in the fact that the application of the release agent to the entire surface of the Tyvek significantly reduces the amount of force necessary to separate the plastic layer from the Tyvek layer. As the plastic layer is peeled back from the Tyvek layer, if too much force is applied the plastic layer completely separates from the Tyvek layer resulting in the possibility that the suture package enclosed therein will fall to the floor. In any event, the complete separation of the plastic layer from the Tyvek layer results in two items to be discarded instead of one, and increases the amount of clutter in the operating room.

A further disadvantage concerns sterilization of the surgical elements packaged within the breather pouch. In general, after the pouch is sealed, the pouch is subjected to a sterilizing gas which passes through the fibrous Tyvek layer. In the prior art, the pouches having adhesive material coating the entire surface of the Tyvek suffer decreased porosity, and accordingly, require longer sterilization times.

A final significant disadvantage lies in the fact that the surgical element may adhere to the adhesive coating during storage, due to storage pressures and temperatures resulting from stacking on shelves or in warehouses. In addition, if the temperatures are too high during the heat sealing process, the surgical element may adhere to the Tyvek layer.

The novel breather pouch for surgical element packages such as sutures and suture-needle assemblies of the present invention obviates the disadvantages encountered in the prior art and provides a breather pouch which substantially reduces or eliminates fiber-pull associated with the prior art. The breather pouch of the present invention overcomes the fiber-pull problem without unduly increasing the cost of the package and further provides a pouch which separates easily to reveal the package enclosed therein without completely separating the plastic layer from the fibrous layer to reduce the amount of clutter in an operating room.

SUMMARY OF THE INVENTION

The present invention provides a novel breather pouch for packaging and displaying surgical instruments, and in particular suture and suture-needle packages, in which the breather pouch is easily openable through the separation of the upper clear plastic layer from the lower layer of fibrous material. The present invention eliminates the problem of fiber-pull during opening in which the fibrous layer in effect delaminates or separates from itself which results in the continued encapsulation of the packaged suture or suture-needle package between the fibrous material and the plastic cover layer. The present invention also provides a breather pouch which is easily opened but which remains as a single entity even after the suture package is removed therefrom.

The breather package of the present invention essentially comprises a sheet of fibrous material such as Tyvek which is provided with a strip of release agent material along each of its longitudinal edges. A clear plastic sheet corresponding substantially in size to the Tyvek sheet is placed over the Tyvek sheet with a suture package positioned therebetween. The plastic layer is then heat sealed to the Tyvek layer along the longitudinal edges at the release agent material, and is further sealed along the bottom edge directly to the Tyvek material as well as along a top edge which is spaced from the edge of the Tyvek to provide a gripping portion to facilitate separation of the two layers to open the pouch.

Since the transverse top seal is spaced from the edges of the Tyvek and plastic sheets, the possibility of fiber-pull along this edge is essentially eliminated since fiber-pull generally occurs at the edge of the Tyvek. As the top seal is peeled apart, the release agent along the longitudinal edges facilitates opening of the package and substantially eliminates the possibility of fiber-pull along the side edges, by providing a pull-force which is substantially less than the force required to separate the Tyvek fibers from themselves. Also, as a result of the application of the release agent to the side edges, the pull force at the top and bottom seals required to separate the plastic layer from the Tyvek layer is slightly greater than the pull force required to separate the two layers at the side edges. Thus, after the initial pull separates the sheets at the top seal, it is easier to open the rest of the package by pulling the sheets apart since the force required to separate the sheets at the longitudinal edges is less than the force required to separate the initial top heat seal.

As the pouch is completely opened to reveal the suture package enclosed therein, the bottom transverse seal acts as a stop to prevent the plastic layer from completely separating from the Tyvek layer due to the fact that the force required to overcome the bottom seal is now greater than the force required to open the package along the longitudinal side seals. This stop feature significantly reduces the possibility of the suture package falling to the ground as in the prior art, and also eliminates the additional clutter in the operating room by keeping the breather pouch intact as a single discardible unit as opposed to having two pieces to discard.

The present invention is formed on an apparatus which feeds a web of Tyvek material having at least two continuous longitudinally directed strips of release agent material applied thereon at regular intervals starting at the first edge of the web and terminating at the second longitudinal edge. The apparatus feeds the web of Tyvek material and a web of plastic material, preferably polyethylene, to a position to enclose suture packages placed in rows between the plastic and Tyvek layers. This assembly is then fed to a heat seal device which simultaneously provides transverse and longitudinal heat seals to seal the suture packages between the two layers.

Preferably, the plastic web is vacuum formed to provide recesses or pockets to accept the suture packages thereon. The Tyvek then overlays the plastic and suture packages and the heat seal device seals about the recesses. Alternately, the release agent material may be positioned in longitudinal strips between the Tyvek and plastic layers prior to the heat sealing step, so that the heat seal is through the release agent between the two layers of material. It is preferred, however, that the release agent material be applied directly to the Tyvek layer.

A heat seal platen is applied to the webs to form the seals for adjacent packages. The assembly is then advanced to a cutter mechanism which cuts the pouches just below the transverse seal to form the bottom of one package and along the longitudinal seals, while ensuring that the top edge seals of the individual packages include the gripping tab formed for each package which facilitates separation of the plastic layer from the Tyvek layer to open the pouch.

BRIEF DESCRIPTION OF THE DRAWINGS

The foregoing features of the present invention will become more readily apparent and may be understood by referring to the following detailed description of an illustrative embodiment of the breather pouch for surgical suture packages and the apparatus for constructing such a package, taken in conjunction with the accompanying drawings in which:

FIG. 3 illustrates a top plan view of a package for surgical elements according to the present invention;

FIGS. 4 and 5 illustrate a plan view of a package according to the present invention in the partially opened and fully opened position, respectively.

DETAILED DESCRIPTION OF THE PREFERRED EMBODIMENTS

Figure 1:
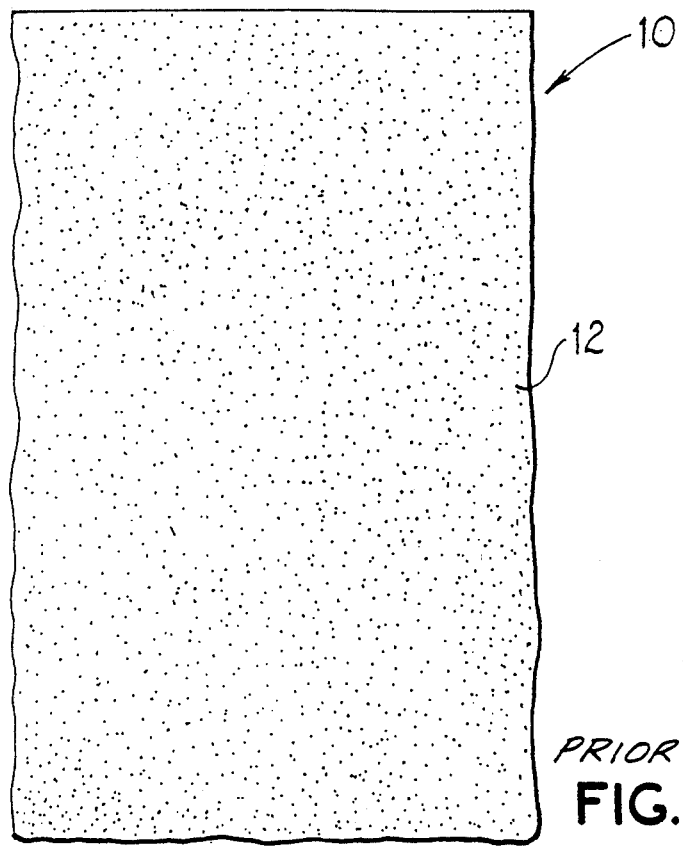
FIG. 1 shows a portion of a web of fibrous material having a release agent material coated thereon as is common in the prior art.

Referring now in specific detail to the drawings, in which like reference numerals identify similar or identical elements throughout the several views, FIG. 1 shows a partial view of a web 10 of fibrous material for use in constructing the package in the prior art. Web 10 is coated over its entire surface with a release agent material 12 which is non-tacky when dry but which covers the entire surface of web 10.

Figure 2:
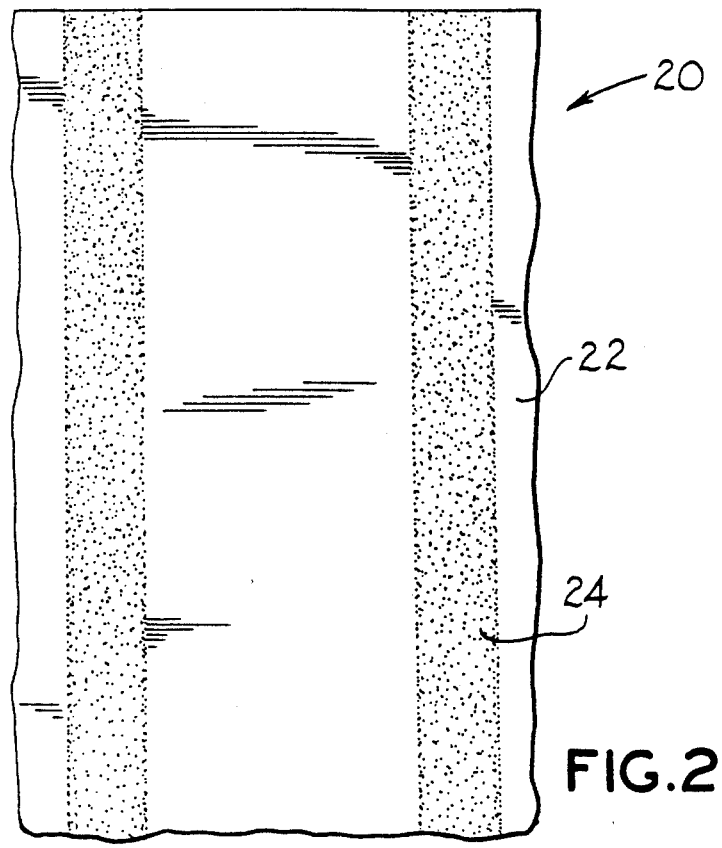
FIG. 2 shows a portion of a web of fibrous material according to the present invention having longitudinal strips of release agent applied thereon.

According to the present invention, as best seen in FIG. 2, a web of fibrous material, preferably a spun-bonded polyolefin fiber material such as Tyvek (registered trademark of DuPont), is provided with strips of release agent material 24 applied at regular intervals on surface 22 of web 20. Web 20 is provided with at least two strips of release agent material, and in the preferred form, web 20 is provided with the regularly spaced strips of release agent material 24 beginning at a first longitudinal edge and terminating at a second longitudinal edge of web 20 such that the strips are parallel to each other. The use of web 20 will be described in greater detail below. Web 20 may consist of Tyvek or any other fibrous material such as cardboard, paperboard, or the like.

FIG. 3 illustrates a package 30 according to the present invention which essentially comprises a breather pouch which displays a surgical element such as suture package 32. Package 30 essentially comprises a sheet of Tyvek material upon which is positioned surgical element 32 which is then sealed by a cover sheet of plastic material which is heat sealed to the Tyvek to provide a suitable display package.

FIGS. 4 and 5 show the package 30 of the present invention with the surgical element 32 removed for purposes of providing clarity to the drawings. Package 30 comprises a sheet of plastic material 34, preferably a polyethylene material, which overlays a sheet of fibrous material 36, which is preferably constructed of Tyvek. Sheet 36 is provided with strips of release agent material 40 which is applied to the longitudinal side edges of sheet 36. Release agent 40 is preferably an adhesive material, such as a water based adhesive, which dries to a non-tacky finish.

After a surgical element such as element 32 is positioned on sheet 36 between strips 40, a sheet of plastic material 34 is positioned in overlying relation to sheet 36 and heat sealed thereto. Plastic sheet 34 is sealed to fiber sheet 36 along longitudinal side seals 42, which seals the plastic sheet 34 to the fibrous sheet 36 at the release agent 40. The package is also sealed by transverse heat seals 44 and 46 which provide a direct seal between the plastic layer 34 and the fibrous layer 36.

In order to open package 30, a gripping tab 38 is provided by positioning top edge seal 44 at a slight distance from the upper edge of the package to allow for ease in gripping the two sheets. Sheet 34 is substantially the same size as sheet 36, but is preferably slightly shorter at top edge 37 to facilitate separation. Fibrous layer 36 is gripped above seal 44, and tab 38 is grasped to pull layer 34 away from layer 36. As the two sheets of material are separated, the surgical element 32 may be removed from the pocket formed therebetween.

The provision of the release agent strips 40 eliminates the possibility of fiber-pull along the longitudinal edges of the package, by providing for a pull force to separate the plastic from the Tyvek which is less than the force required to separate the fibers in the Tyvek from themselves. The force required to separate sheet 34 from sheet 36 at top seal 44 is greater than the force necessary to separate the sheets at seal 42. Thus, after the initial pull to open the package at heat seal 44, it is easier to separate sheet 34 from sheet 36 along longitudinal heat seal 42. On the other hand, since heat seal 46 at the bottom of the package is a seal directly between the plastic layer 34 and the fibrous layer 36, it provides a stop feature to prevent complete separation of the two layers upon opening of the package. Heat seal 46 requires a pull force which is greater than the pull force required to separate sheet 34 from sheet 36 at the longitudinal seals 42.

Preferably, the force required to separate plastic sheet 34 from fibrous sheet 36 at seals 44 and 46 is slightly greater than the force required to separate the sheets at seals 42, so that for the preferred Tyvek-polyethylene pouch the force at seals 44 and 46 may be slightly greater than about 1 lb/inch, for example, between 1 lb/inch and 2 lbs/inch, while the force at seals 42 is preferably no greater than about 1 lb/inch.

Figure 6:
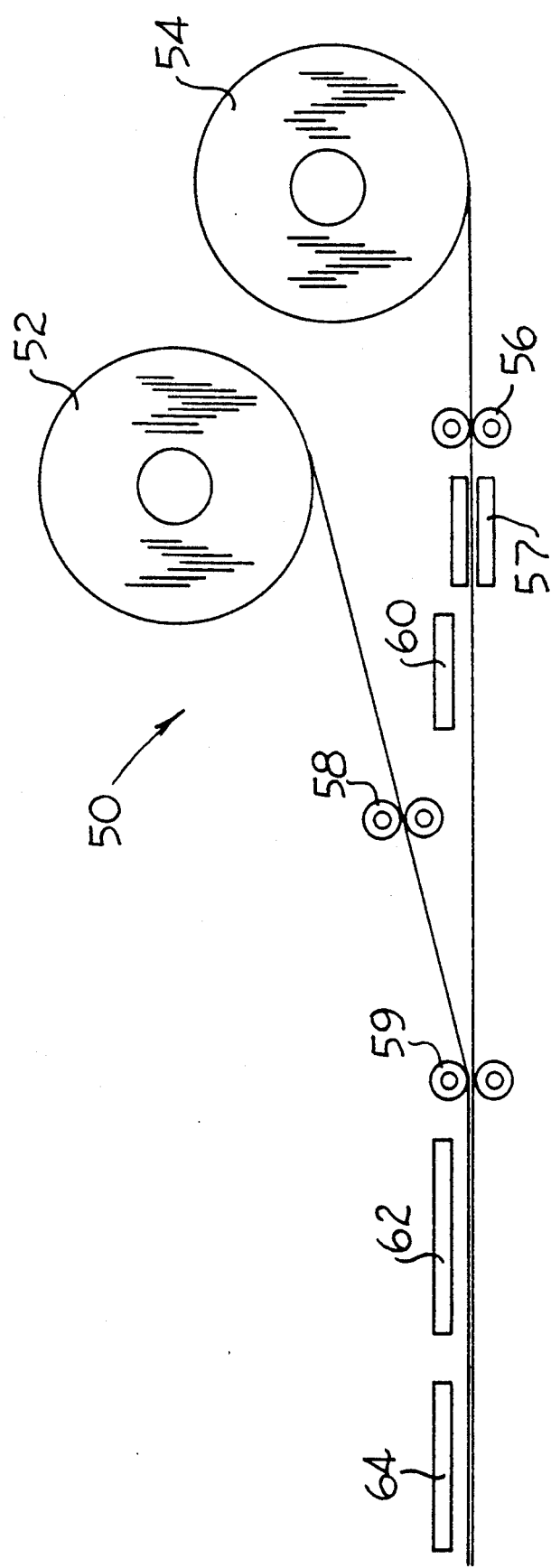
FIG. 6 illustrates a schematic view of an apparatus for assembling the package of the present invention.

FIG. 6 illustrates an apparatus for assembling package 30 of the present invention. Apparatus 50 provides a web of fibrous material 52 which is similar to the web 20 as shown in FIG. 2, in which at least two longitudinal strips of release agent material are applied thereon. Web 54 comprises a web of plastic material, preferably polyethylene, and web 54 is advanced by advancing means 56 to a vacuum device 57 which forms recesses for accepting surgical elements to be packaged. Surgical elements such as suture or suture-needle assembly packages are placed in spaced relation in the recesses, which are positioned in relation to web 52 between the longitudinal strips of release agent material on web 52 by placement means 60. Web 52 is advanced by advancement means 58 to a heat sealing station along with web 54, and the two webs are then advanced by advancement means 59. Heat sealing station 62 provides longitudinal heat seals which correspond in position to the strips of release agent material, while also providing the transverse heat seal which corresponds to the top and bottom of the packages. The webs are then advanced to cutting station 64 which provides transverse and longitudinal cuts to separate adjacent packages at the transverse and longitudinal heat seals which form the individual packages. The cut at the top seal is preferably made a distance from the seal so as to provide a gripping tab at the top of the package to facilitate opening the package.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto are to be considered within the scope of the invention.

What is claimed is:

1. A package for surgical elements comprising:
   a sheet of fibrous material having longitudinal side edges and top and bottom transverse edges,
   a sheet of plastic material having longitudinal side edges and top and bottom transverse edges, said plastic overlaying and corresponding substantially in size and shape to said fibrous sheet, and
   a release agent material positioned between said sheets along each longitudinal side edge of said sheets,
   wherein said plastic sheet is heat sealed to said fibrous sheet along said top and bottom edges, and is further heat sealed to said fibrous sheet along said longitudinal side edges at said release agent.

2. A package according to claim 1, wherein said release agent material is applied as a strip along each longitudinal side edge of said fibrous sheet.

3. A package according to claim 1, wherein said sheet of fibrous material comprises spun-bonded polyolefin fibers.

4. A package according to claim 1, wherein said sheet of plastic material comprises polyethylene.

5. A package according to claim 1, wherein said sheet of fibrous material comprises laminated layers of fibers.

6. A package according to claim 1, wherein a pull force required to separate said fibrous sheet from said plastic sheet at said transverse top and bottom edges is greater than a pull force required to separate said fibrous sheet from said plastic sheet through said release agent at said longitudinal edges.

7. A package according to claim 1, wherein said release agent comprises an adhesive layer.

8. A package according to claim 6 wherein said pull force at said top and bottom edges is between about 1 and 2 lbs/in., and said pull force at said longitudinal edges through said release agent is no greater than about 1 lbs/in.

9. A package according to claim 1, wherein said heat seal at said top edge is spaced from said top edge to define a gripping tab for separating said sheets.

10. A package for surgical suture-needle assemblies, said package comprising:
 a sheet of fibrous material having top and bottom transverse edges, and longitudinal side edges;
 a sheet of plastic material corresponding in size and shape to said fibrous sheet, said plastic material having a top and bottom transverse edge, and longitudinal side edges; and
 a strip of release agent material positioned between said sheets at each of said longitudinal side edges of said sheets;
 wherein said plastic sheet is adhered to said fibrous sheet along said side edges at said strips of release agent material, along said bottom edge, and parallel to but spaced a distance from said top edge to define a gripping tab to facilitate separation of said plastic sheet from said fibrous sheet, said suture assemblies being secured in a pocket formed between said fibrous sheet and said plastic sheet.

11. A package according to claim 10, wherein a pull force required to separate said plastic sheet from said fibrous sheet at said top and bottom edges is greater than a pull force required to separate said plastic sheet from said fibrous sheet at said side edges.

12. A package according to claim 10, wherein said release agent material is applied as a strip along each longitudinal side edge of said fibrous sheet.

13. A package according to claim 10, wherein said release agent comprises an adhesive material, said plastic sheet being adhered to said fibrous sheet through said adhesive material along said longitudinal edges, and said adhesive material being adhered to said fibrous material.

14. A package according to claim 10, wherein said fibrous material comprises spun-bonded polyolefin fibers.

15. A package according to claim 10, wherein said plastic material comprises polyethylene.

16. A breather pouch for a surgical elements, comprising:
 a sheet of fibrous material having top and bottom transverse edges, and longitudinal side edges;
 a sheet of plastic material having top and bottom transverse edges and longitudinal side edges, said plastic sheet corresponding substantially in size and shape to said fibrous sheet; and
 a release agent material being positioned between said sheets at each of said longitudinal edges of said sheets;
 wherein said surgical elements are sealed between said fibrous sheet and said plastic sheet by a transverse heat seal along said bottom edges between said plastic and fibrous sheets, a transverse heat seal adjacent said top edges between said plastic and fibrous sheets, and longitudinal heat seals along said side edges which seal said plastic sheet to said fibrous sheet at said release agent.

17. A breather pouch according to claim 16, wherein said release agent material is applied as a strip along each longitudinal side edge of said fibrous sheet.

18. A breather pouch according to claim 16, wherein said transverse seal adjacent said top edge is spaced from said top edge so as to provide a gripping tab to facilitate separating said sheets to open said pouch.

19. A breather pouch according to claim 16, wherein said plastic material comprises polyethylene.

20. A breather pouch according to claim 16, wherein said fibrous material comprises spun-bonded polyolefin fibers.

21. A breather pouch according to claim 16, wherein said release agent comprises an adhesive.

22. A breather pouch according to claim 18, wherein a pull force required to separate said plastic sheet from said fibrous sheet at said top and bottom seals is greater than a pull force required to separate said sheets at said longitudinal side seals.

23. A breather pouch according to claim 16, wherein said surgical elements comprise suture-needle assemblies.

24. A breather pouch according to claim 16, wherein a pull force required to separate said plastic sheet from said fibrous sheet at said longitudinal side edges at said release agent material is less than a pull force required to separate fibers of said fibrous sheet from themselves.

25. A method of opening a breather pouch having surgical elements packaged therein, said breather much including a sheet of fibrous material having top and bottom transverse edges, and longitudinal side edges; a sheet of plastic material having top and bottom transverse edges and longitudinal side edges, said plastic sheet corresponding substantially in size and shape to said fibrous sheet; a release agent material being positioned between said sheets at each of said longitudinal edges of said sheets; said surgical elements being sealed between said fibrous sheet and said plastic sheet by a transverse heat seal along said bottom edges directly between said plastic and fibrous sheets, a transverse heat seal parallel to and spaced from said top edges to form a fibrous and a plastic gripping tab, said transverse heat seal being directly between said plastic and fibrous sheets, and longitudinal heat seals along said side edges which seal said plastic sheet to said fibrous sheet at said release agent; said method comprising the steps of:
 grasping said fibrous sheet with one hand at said fibrous gripping tab;
 grasping said plastic sheet with another hand at said plastic gripping tab;
 applying a first pull force sufficient to overcome said top transverse heat seal to separate said fibrous sheet from said plastic sheet;
 applying a second pull force sufficient to overcome said longitudinal side heat seals to continue separation of said fibrous sheet from said plastic sheet; and
 removing said surgical element from said breather pouch.

26. A method according to claim 25, wherein said first pull force is greater than said second pull force.

27. A method according to claim 25, further comprising discontinuing said application of said second pull force upon reaching said bottom transverse heat seal.

* * * * *